US00PP13615P29

(12) United States Plant Patent
Huber

(10) Patent No.: US PP13,615 P2
(45) Date of Patent: Mar. 4, 2003

(54) SPIRAEA PLANT NAMED 'GOLDEN CARPET'

(76) Inventor: Tony Huber, 4137 2e Rue, Chomedey, Laval, Quebec (CA), H7W 2N2

( * ) Notice: Subject to any disclaimer, the term of this patent is extended or adjusted under 35 U.S.C. 154(b) by 0 days.

(21) Appl. No.: 10/036,935

(22) Filed: Dec. 31, 2001

(51) Int. Cl.[7] ..... A01H 5/00

(52) U.S. Cl. ..... Plt./226
(58) Field of Search ..... Plt./226

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Spiraea plant named 'Golden Carpet', characterized by its compact, and low mounding plant habit; dense and bushy growth habit; and small yellow-colored leaves.

1 Drawing Sheet

BOTANICAL CLASSIFICATION/CULTIVAR DESIGNATION

*Spiraea×bumalda* cultivar Golden Carpet.

BACKGROUND OF THE INVENTION

The present Invention relates to a new and distinct cultivar of Spiraea plant, botanically known as *Spiraea× bumalda,* and hereinafter referred to by the cultivar name Golden Carpet.

The new Spiraea is a product of a planned breeding program conducted by the Inventor in Boisbriand, Quebec, Canada. The objective of the breeding program is to create compact Spiraeas with unique leaf coloration and few to no flowers.

The new Spiraea originated from a cross made by the Inventor of a proprietary Spiraea selection identified as code number G-DW-80-48, not patented, as the female, or seed parent, with a proprietary Spiraea selection identified as code number G-DW-80-106, not patented, as the male, or pollen parent. The new Spiraea was first observed in 1982 and was selected in 1984 as a single plant from the resulting progeny by the Inventor in a controlled environment in Boisbriand, Quebec, Canada, on the basis of its yellow-colored foliage.

Asexual reproduction of the new cultivar by terminal cuttings taken in a controlled environment in Boisbriand, Quebec, Canada since 1984, has shown that the unique features of this new Spiraea are stable and reproduced true to type in successive generations.

SUMMARY OF THE INVENTION

Plants of the cultivar Golden Carpet have not been observed under all possible environmental conditions. The phenotype may vary somewhat with variations in environment and culture such as temperature, light intensity and daylength without, however, any variance in genotype.

The following traits have been repeatedly observed and are determined to be the unique characteristics of 'Golden Carpet'. These characteristics in combination distinguish 'Golden Carpet' as a new and distinct cultivar:

1. Compact, and low mounding plant habit.
2. Dense and bushy growth habit.
3. Small yellow-colored leaves.

Plants of the new Spiraea differ from plants of the parents and the cultivars Green Carpet, U.S. Plant patent application Ser. No. 10/036,936 filed concurrently, and Sparkling Carpet, U.S. Plant patent application Ser. No. 10/036,937 filed concurrently, primarily in foliage color.

Plants of the new Spiraea are similar in foliage color to plants of the Spiraea 'Gold Mound', not patented. In side-by-side comparisons conducted in Boisbriand, Quebec, Canada, plants of the new Spiraea differed from plants of the cultivar Gold Mound in the following characteristics:

1. Plants of the new Spiraea were more compact than plants of the cultivar Gold Mound.
2. Plants of the new Spiraea were more freely branching and bushier than plants of the cultivar Gold Mound.
3. Plants of the new Spiraea had smaller leaves than plants of the cultivar Gold Mound.
4. Plants of the new Spiraea produced no or only a few flowers whereas plants of the cultivar Gold Mound produced numerous flowers.

Plants of the new Spiraea are also similar in foliage color to plants of the Spiraea 'Golden Princess', not patented. In side-by-side comparisons conducted in Boisbriand, Quebec, Canada, plants of the new Spiraea differed from plants of the cultivar Golden Princess in the following characteristics:

1. Plants of the new Spiraea were more compact than plants of the cultivar Golden Princess.
2. Plants of the new Spiraea were more freely branching and bushier than plants of the cultivar Golden Princess.
3. Plants of the new Spiraea had smaller leaves than plants of the cultivar Golden Princess.
4. Plants of the new Spiraea produced no or only a few flowers whereas plants of the cultivar Golden Princess produced numerous flowers.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Spiraea.

The photograph comprises a side perspective view of a typical three-year old plant of 'Golden Carpet' grown in an outdoor nursery in Boisbriand, Quebec, Canada.

DETAILED BOTANICAL DESCRIPTION

In the following description, color references are made to The Royal Horticultural Society Colour Chart except where general terms of ordinary dictionary significance are used. Plants grown in an outdoor nursery under full sunlight conditions and commercial production conditions in Boisbriand, Quebec, Canada for about three years were used for the following description.

Botanical classification: *Spiraea×bumalda* cultivar Golden Carpet.

Parentage:

*Female parent.*—Proprietary *Spiraea×bumalda* selection identified as G-DW-80-48, not patented.

*Male parent.*—Proprietary *Spiraea×bumalda* selection identified as G-DW-80-106, not patented.

Propagation:

*Type cutting.*—Terminal cuttings.

*Time to initiate roots.*—About 21 to 28 days at 20° C.

*Time to produce a rooted cutting.*—About 5 to 8 weeks at 24 to 28° C.

*Root description.*—Fine, fibrous.

*Rooting habit.*—Freely branching.

Plant description:

*Form.*—Compact perennial deciduous shrub; dense and low mounded plant habit. Freely branching; lateral branches potentially forming at every node.

*Plant height.*—About 20 cm.

*Plant diameter.*—About 38 cm.

*Vigor.*—Vigorous.

*Lateral branch description.*—Length: About 6.9 cm. Diameter: About 0.9 mm. Internode length: About 8 mm. Strength: Weak. Texture: Glabrous. Color: 177B.

*Foliage description.*—Leaves simple, alternate, generally symmetrical. Length: About 3.1 cm. Width: About 1.4 cm. Shape: Lanceolate. Apex: Acute. Base: Acute. Margin: Serrate. Texture, upper and lower surfaces: Smooth, glabrous. Venation pattern: Pinnate. Color: Developing foliage, upper surface: 10A to 13C; 144B along veins. Developing foliage, lower surface: 13C. Fully expanded foliage, upper surface: 153D. Fully expanded foliage, lower surface: 153D; 147C along veins. Venation, upper surface: 2D to 4D. Venation, lower surface: 153D. Petiole length: About 2.1 cm. Petiole diameter: About 0.7 mm. Petiole texture: Smooth. Petiole color: 153D.

Flower description:

*Flower type and habit.*—Few to no flowers. Small single flowers arranged in corymbs; flowers face mostly upright. Flowers self-cleaning.

*Natural flowering season.*—June to September in Quebec, Canada; flowering sporadic.

*Flower longevity on the plant.*—About four days.

*Fragrance.*—None detected.

*Inflorescence diameter.*—About 2.1 cm.

*Inflorescence height.*—About 1.9 cm.

*Flowers.*—Quantity per inflorescence: About 14. Appearance: Rotate, five-parted. Diameter: About 6.6 mm. Depth: About 2 mm.

*Flower buds* (*showing color*).—Length: About 2.3 mm. Diameter: About 1.7 mm. Shape: Oblong, rounded. Color: 62C.

*Petals.*—Quantity per flower: Five. Length: About 2.5 mm. Width: About 2.3 mm. Shape: Rounded. Apex: Rounded. Base: Attenuate. Margin: Entire. Texture, upper and lower surfaces: Smooth. Color: When opening, upper surface: 58D; towards margins and veins, 54B. When opening, lower surface: 63D; towards margins, 54A to 54B. Fully opened, upper surface: 62B; fading to 62D with subsequent development. Fully opened, lower surface: 62C.

*Sepals.*—Quantity per flower: Five. Calyx length: About 1.4 mm. Calyx diameter: About 1.6 mm. Shape: Deltoid. Apex: Acute or slightly mucronate. Margin: Entire. Texture: Upper surface, glabrous; lower surface, slightly pubescent. Color: Upper surface: Towards base, 151A; towards apex, 152B. Lower surface: 152C.

*Peduncles.*—Length: About 9.7 mm. Diameter: About 0.7 mm. Angle: About 47° from the stem. Strength: Flexible, moderately strong. Color: 146D.

*Pedicels.*—Length: About 3.7 mm. Diameter: About 0.4 mm. Angle: About 47° from the stem. Strength: Flexible, moderately strong. Color: 144A to 144B.

*Reproductive organs.*—Stamens: Quantity per flower: About 26. Anther shape: Bi-lobed. Anther length: About 0.5 mm. Anther color: 63D. Pollen amount: Moderate. Pollen color: 155C. Pistils: Quantity per flower: About four or five. Pistil length: About 2.7 mm. Stigma shape: Slightly club-shaped. Stigma color: 145D. Style length: About 1.1 mm. Style color: 49D. Ovary color: 145D.

*Seed/fruit.*—Seed and fruit production has not been observed.

Disease pest resistance: Plants of the new Spiraea have not been noted to be resistant to pathogens or pests common to Spiraea.

Weather tolerance: Plants of the new Spiraea have been observed to be tolerant to rain and wind.

It is claimed:

1. A new and distinct cultivar of Spiraea plant named 'Golden Carpet', as illustrated and described.

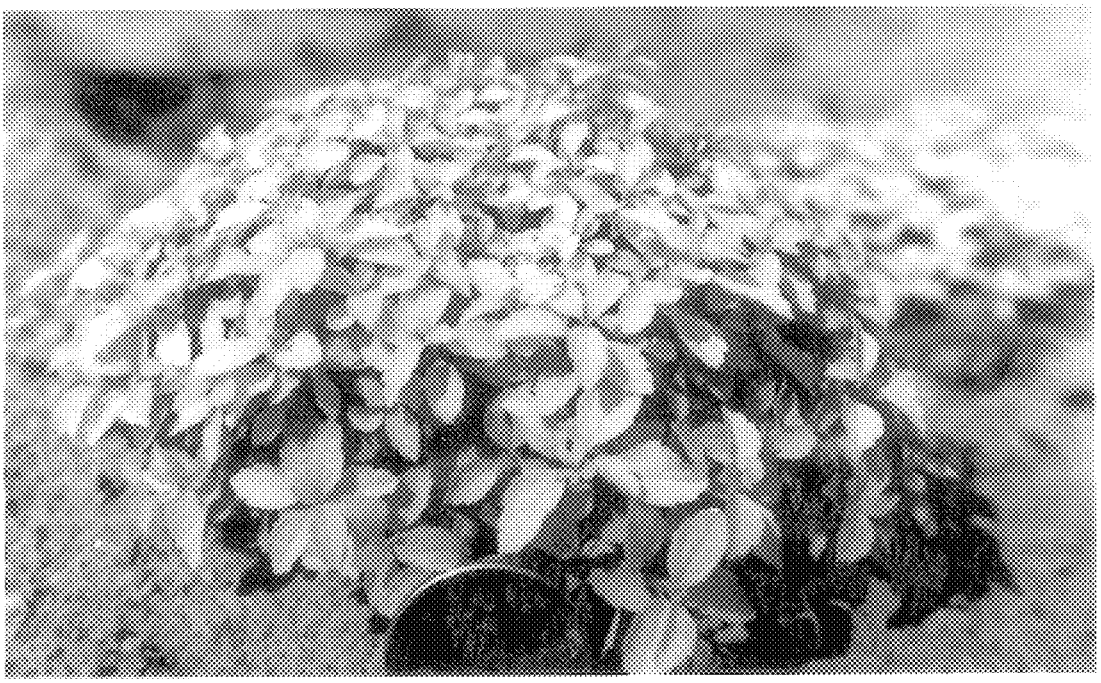

* * * * *